US010597706B2

(12) United States Patent
Toloue et al.

(10) Patent No.: US 10,597,706 B2
(45) Date of Patent: Mar. 24, 2020

(54) METHODS AND KITS FOR REDUCING ADAPTER-DIMER FORMATION

(71) Applicant: BIOO SCIENTIFIC CORPORATION, Austin, TX (US)

(72) Inventors: Masoud Toloue, Austin, TX (US); Adam R. Morris, Austin, TX (US); Kevin D. Allen, Austin, TX (US)

(73) Assignee: BIOO Scientific Corporation, Austin, TX (US)

(*) Notice: Subject to any disclaimer, the term of this patent is extended or adjusted under 35 U.S.C. 154(b) by 239 days.

(21) Appl. No.: 15/354,491

(22) Filed: Nov. 17, 2016

(65) Prior Publication Data

US 2017/0137875 A1 May 18, 2017

Related U.S. Application Data

(60) Provisional application No. 62/256,662, filed on Nov. 17, 2015.

(51) Int. Cl.
*C12Q 1/6855* (2018.01)
*C12Q 1/6874* (2018.01)
*C12N 9/00* (2006.01)

(52) U.S. Cl.
CPC ......... *C12Q 1/6855* (2013.01); *C12Q 1/6874* (2013.01)

(58) Field of Classification Search
CPC ............ C12Q 1/6855; C12Q 2521/107; C12Q 2521/501; C12Q 1/6874
See application file for complete search history.

(56) References Cited

U.S. PATENT DOCUMENTS

| | | |
|---|---|---|
| 5,691,136 A | 11/1997 | Lupski et al. |
| 2012/0322691 A1 | 12/2012 | Sachidanandam et al. |
| 2013/0157869 A1 | 6/2013 | McReynolds et al. |
| 2014/0128292 A1 | 5/2014 | Toloue et al. |
| 2014/0234846 A1 | 8/2014 | Piepenburg et al. |

FOREIGN PATENT DOCUMENTS

WO WO-2008/097957 A2 8/2008

OTHER PUBLICATIONS

Jayaprakash, A.D. et al., Identification and remediation of biases in the activity of RNA ligases in small-RNA deep sequencing, Nucl. Acids Res., vol. 39, e141, pp. 1-12, (Year: 2011).*
Lu, C. et al., Construction of small RNA cDNA libraries for deep sequencing, *Methods* 43: 110-117, 2007.

\* cited by examiner

*Primary Examiner* — Teresa E Strzelecka
(74) *Attorney, Agent, or Firm* — Julie K. Staple; Dinsmore & Shohl LLP

(57) ABSTRACT

The current teachings relate to methods for reducing adapter-dimer formation, particularly when preparing nucleic acids of interest for subsequent amplification and/or sequencing. Also described are kits for use in performing certain disclosed methods.

14 Claims, 7 Drawing Sheets

Specification includes a Sequence Listing.

FIG. 4A  FIG. 4B
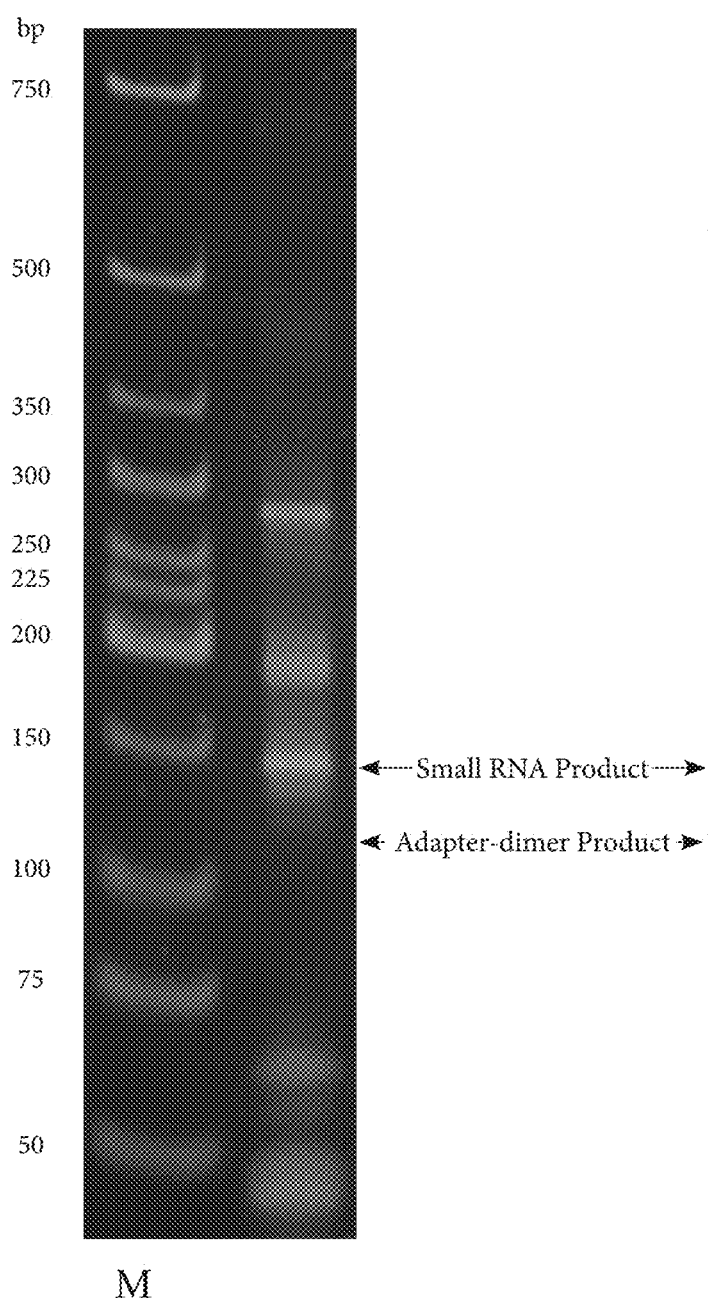
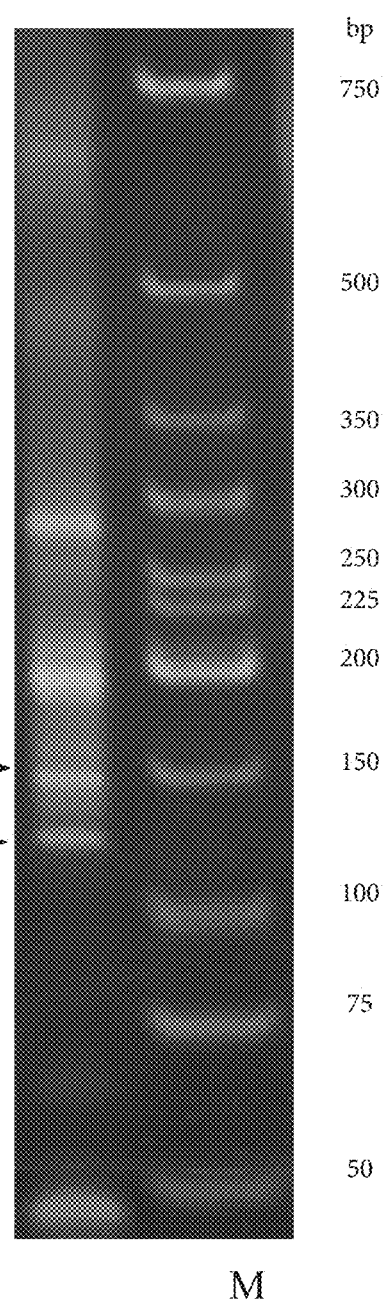

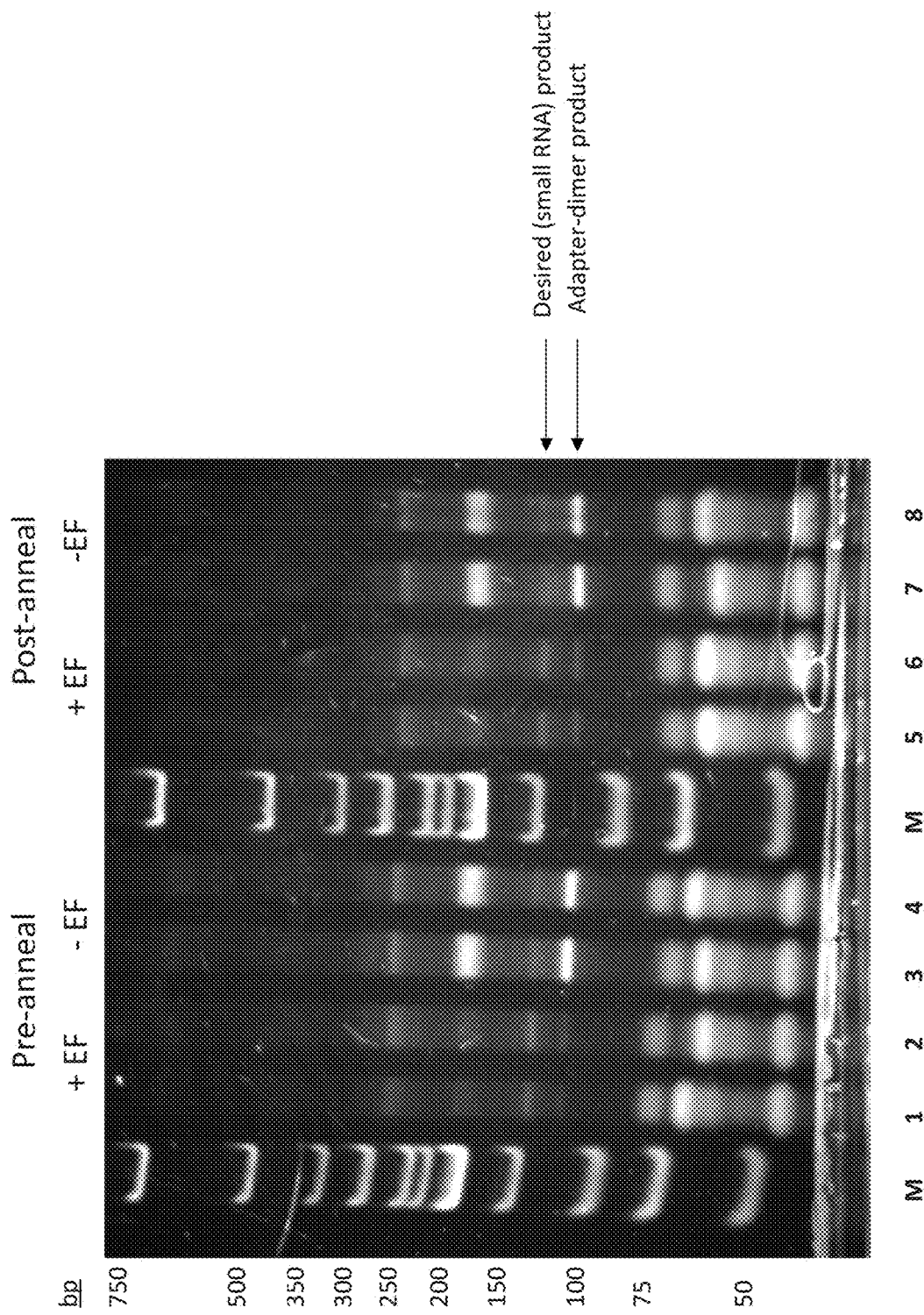

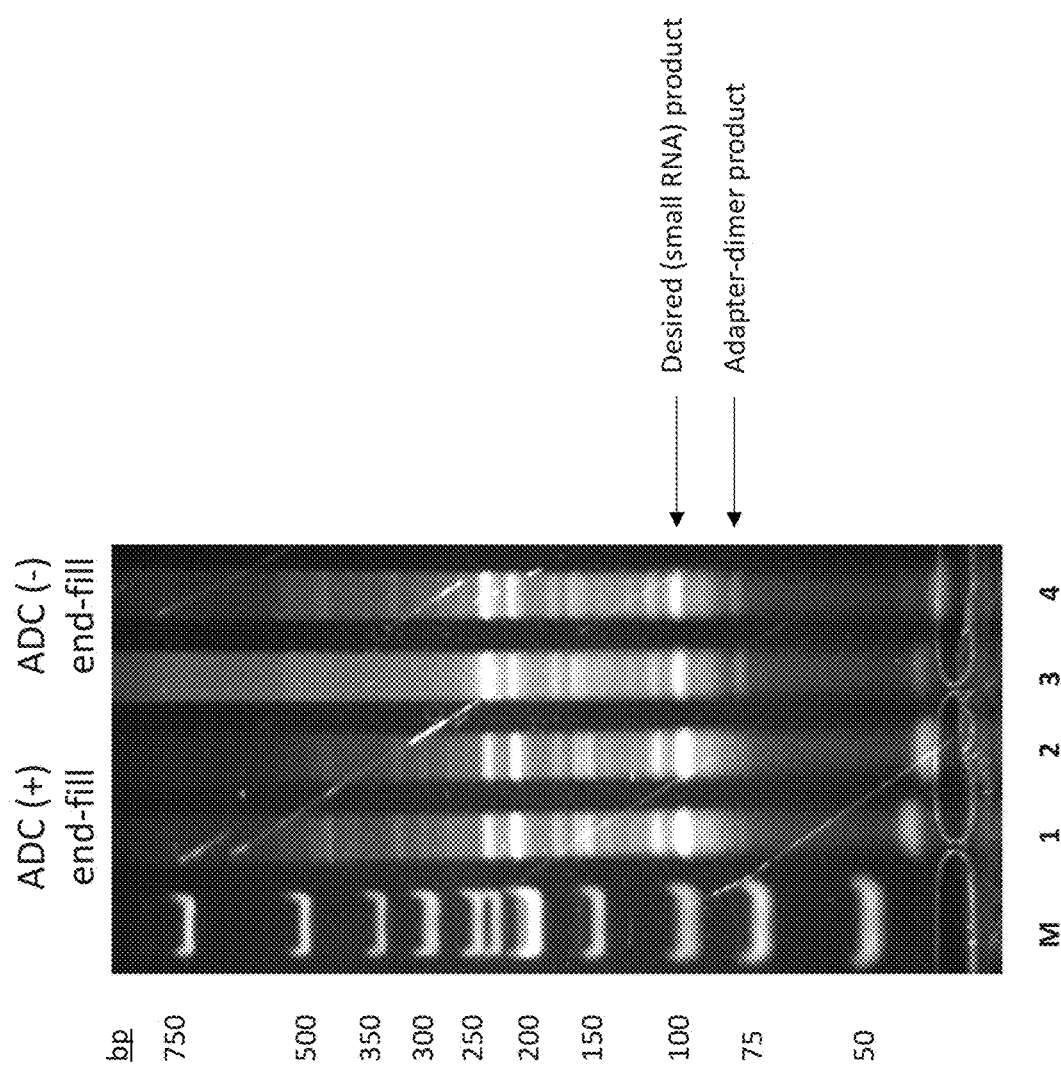

SEQUENCE LISTING

<160> NUMBER OF SEQ ID NOS: 6

<210> SEQ ID NO 1

-continued

```
<211> LENGTH: 25
<212> TYPE: DNA
<213> ORGANISM: Artificial Sequence
<220> FEATURE:
<223> OTHER INFORMATION: Synthetic: 3' NEXTFLEX 4N Adenylated Adapter
<220> FEATURE:
<221> NAME/KEY: misc_feature
<223> OTHER INFORMATION: rApp on 5' end and ddC on 3' end
<220> FEATURE:
<221> NAME/KEY: misc_feature
<222> LOCATION: (1)..(4)
<223> OTHER INFORMATION: n is a, c, g, or t

<400> SEQUENCE: 1
nnnntggaat tctcgggtgc caagg                                         25

<210> SEQ ID NO 2
<211> LENGTH: 30
<212> TYPE: RNA
<213> ORGANISM: Artificial Sequence
<220> FEATURE:
<223> OTHER INFORMATION: Synthetic: 5' NEXTFLEX 4N Adapter
<220> FEATURE:
<221> NAME/KEY: misc_feature
<222> LOCATION: (27)..(30)
<223> OTHER INFORMATION: n is a, c, g, or u

<400> SEQUENCE: 2
guucagaguu cuacaguccg acgaucnnnn                                    30

<210> SEQ ID NO 3
<211> LENGTH: 22
<212> TYPE: DNA
<213> ORGANISM: Artificial Sequence
<220> FEATURE:
<223> OTHER INFORMATION: Synthetic: NEXTFLEX RT Primer

<400> SEQUENCE: 3
gccttggcac ccgagaattc ca                                            22

<210> SEQ ID NO 4
<211> LENGTH: 63
<212> TYPE: DNA
<213> ORGANISM: Artificial Sequence
<220> FEATURE:
<223> OTHER INFORMATION: Synthetic: NEXTFLEX Barcode Primer
<220> FEATURE:
<221> NAME/KEY: misc_feature
<222> LOCATION: (25)..(30)
<223> OTHER INFORMATION: "nnnnnn" can be CGTGAT, ACATCG, GCCTAA, TGGTCA,
      CAGTGT, ATTGGC, GATCTG, TCAAGT, CTGATC, AAGCTA, GTAGCC, TACAAG,
      TTGACT, GGAACT, TGACAT, GGACGG, CTCTAC, or GCGGAC.
<220> FEATURE:
<221> NAME/KEY: misc_feature
<222> LOCATION: (25)..(30)
<223> OTHER INFORMATION: "nnnnnn" can also be TTTCAC, GGCCAC, GGAAAC,
      CGTACG, CCACTC, GCTACC, ATCAGT, GCTCAT, AGGAAT, CTTTTG, TAGTTG,
      CCGGTG, ATCGTG, TGAGTG, CGCCTG, GCCATG, AAAATG, TGTTGG, ATTCCG,
      AGCTAG, GTATAG, TCTGAG,

<400> SEQUENCE: 4
caagcagaag acggcatacg agatnnnnnn gtgactggag ttccttggca cccgagaatt   60
cca                                                                 63

<210> SEQ ID NO 5
<211> LENGTH: 50
<212> TYPE: DNA
<213> ORGANISM: Artificial Sequence
<220> FEATURE:
<223> OTHER INFORMATION: Synthetic: NEXTFLEX Universal Primer
```

```
<400> SEQUENCE: 5
aatgatacgg cgaccaccga gatctacacg ttcagagttc tacagtccga                50

<210> SEQ ID NO 6
<211> LENGTH: 21
<212> TYPE: RNA
<213> ORGANISM: Artificial Sequence
<220> FEATURE:
<223> OTHER INFORMATION: Synthetic: microRNA Control
<220> FEATURE:
<221> NAME/KEY: misc_feature
<222> LOCATION: (1)..(1)
<223> OTHER INFORMATION: 5' Phos

<400> SEQUENCE: 6
cucaggaugg cggagcgguc u                                               21
```

METHODS AND KITS FOR REDUCING ADAPTER-DIMER FORMATION

CROSS-REFERENCE TO RELATED APPLICATIONS

This application claims the benefit of U.S. Provisional Application Ser. No. 62/256,662, filed Nov. 17, 2015, entitled "Methods and Kits for Reducing Adapter-Dimer Formation", which is incorporated herein by reference in its entirety.

STATEMENT REGARDING FEDERALLY SPONSORED RESEARCH

This work was performed in part with government support under NSF Phase II Grant No. 1431020. The Government may have certain rights in the claimed inventions.

REFERENCE TO SEQUENCE LISTING SUBMITTED VIA EFS-WEB

This application includes an electronically submitted sequence listing in .txt format. The .txt file contains a sequence listing entitled "BIO019US_ST25.txt" and is 2,490 bytes in size. The sequence listing contained in this .txt file is part of the specification and is hereby incorporated by reference herein in its entirety.

FIELD

The current teachings relate generally to the field of nucleic acid sequencing, particularly to reducing adapter dimer formation. More particularly, the current teachings are directed to improving the creation of sequencing libraries comprising small RNA molecules.

BACKGROUND

Small RNA sequencing using next generation sequencing technologies (sRNA-seq) is invaluable for small RNA profiling and discovery in fields such as cancer, stem cell biology, and epigenetic gene regulation. sRNA-seq library preparation has historically suffered from three major drawbacks; severe bias, the need for gel-based purification, and the lack of low-input protocols. Reducing the formation of adapter-dimer products is a key aspect in the successful creation of these libraries.

The need to purify final small RNA sequencing libraries by gel, typically by PAGE gel, is due to the small difference in the size of adapter-dimer molecules versus insert-containing molecules following the PCR step of library preparation. In typical DNA or RNA library prep, insert-containing molecules are at least 100 bp larger than adapter-dimer molecules, and thus can be removed using Solid Phase Reversible Immobilization (SPRI) magnetic beads. However, since insert-containing molecules are only ~20 bp larger than adapter-dimer molecules in small RNA libraries, SPRI size selection is not feasible, and gel-based selection must be performed. The need for gel-based size selection greatly limits both throughput and automation potential of small RNA library preparation, as only a limited number of libraries can be run on a single gel and it is a labor-intensive process that is not amenable to automation.

The lack of low-input protocols for sRNA-seq is also related to adapter-dimer formation. Small RNA sequencing is somewhat unique in that additional PCR cycles result in negligible bias; thus it should theoretically be possible to create low-input small RNA libraries by using a high number of PCR cycles. However, adapter-dimer present in the libraries will also be greatly amplified, which eventually leads to a library where adapter-dimer products are extremely abundant, making it difficult to isolate insert-containing products and leading to sequencing data where very few of the reads are useful. A number of methods have been developed to reduce adapter-dimer formation in small RNA library preparation, but unfortunately none are effective at reducing adapter-dimer formation to such an extent that gel-free or low-input small RNA library preparation is possible There are currently multiple methods for reduction of adapter-dimer products. In one of these methods, a complementary oligonucleotide is annealed to the 3' adapter following the first ligation step, which converts excess 3' adapter from single-stranded DNA to double-stranded DNA. The double-stranded DNA is a poor substrate for the T4 RNA ligase 1 enzyme used in the subsequent reaction, resulting in reduced formation of adapter-dimer products.

Traditional methods of construction of sRNA libraries have been shown to suffer from severe bias, resulting in final sequencing results that do not accurately represent relative abundances of small RNAs in the starting material. This bias can be greatly reduced through the use of oligonucleotide adapters with randomized bases at the ligation junctions. However, the strategy of hybridization of a complementary oligonucleotide does not work well to reduce adapter-dimer formation when using adapters with randomized ends. Thus, purification of intermediary ligation products by polyacrylamide gel electrophoresis (PAGE) was often used in sRNA library preparation protocols utilizing adapters with randomized ends. Purification of products by PAGE has many disadvantages, so a gel-free adapter-dimer reduction strategy was developed. This strategy requires the use of a proprietary reagent combined with isopropanol and SPRI beads to deplete excess 3' adapter following the first ligation step, thus reducing formation of adapter-dimer in the final library. However, it should be noted that neither this strategy nor strategies using conventional (non-randomized end containing) adapters are typically effective at reducing adapter-dimer formation to such a level that final purification by PAGE can be replaced by a SPRI-based method.

Thus, there is a need for methods for reducing the formation of adapter-dimer products in certain molecular biology techniques, including creating nucleic acid sequencing libraries. For example but not limited to, RNA libraries for use in next generation sequencing of RNA, including small RNA.

SUMMARY

The disclosed teachings provide a dual approach to adapter-dimer reduction, thereby allowing gel-free or low-input small RNA library preparation. The dual approach to adapter-dimer reduction involves first depleting excess unligated 3' adapter through a magnetic-bead based method, and then inactivating any residual 3' unligated adapter with an enzymatic method. This combination of depletion and inactivation of excess unligated 3' adapter results in significant reduction of adapter-dimer formation, allowing gel-free or low input library preparation.

Certain method embodiments for reducing adapter-dimer formation comprise: combining a nucleic acid sample, at least one 3' adapter and at least one first ligase to form a first reaction composition; incubating the first reaction composition under conditions suitable for first ligation products to be generated, to form a second reaction composition comprising first ligation products and at least some un-ligated 3' adapters; combining at least one oligonucleotide comprising a reverse transcription priming site with the second reaction composition to form a third reaction composition; incubating the third reaction composition under conditions suitable for at least some of the oligonucleotides to anneal with at least some of the first reaction products and at least some of the un-ligated 3' adapters to form 3' adapter-oligonucleotide duplexes comprising single-stranded 5' overhang portions; combining at least one DNA polymerase with the third reaction composition and incubating under conditions suitable for the polymerase to convert at least some of the 3' adapter-oligonucleotide duplexes comprising single-stranded 5' overhang portions to double-stranded adapter-oligonucleotide duplexes; adding at least one second ligase and at least one 5' adapter to the third reaction composition comprising double-stranded adapter-oligonucleotide duplexes and first ligation products and incubating under conditions suitable for forming at least some second ligation products, thereby reducing at least some 5' adapter-3' adapter dimer formation.

Certain method embodiments for reducing adapter-dimer formation comprise: combining a sample comprising target nucleic acids, at least one 3' adapter annealed to an oligonucleotide comprising a reverse transcription primer binding site, and at least one first ligase to form a first reaction composition, wherein the 3'adapter annealed with the oligonucleotide comprises a single-stranded 5' overhang portion; incubating the first reaction composition under conditions suitable for first ligation products to be generated, to form a second reaction composition comprising first ligation products and at least some un-ligated 3' adapters annealed to oligonucleotides; combining at least one DNA polymerase with the second reaction composition and incubating under conditions suitable for the polymerase to convert at least some of the single-stranded 5' overhang portions of the 3' adapters annealed to the oligonucleotides to double-stranded adapter-oligonucleotide duplexes lacking overhang portions; and combining at least one second ligase and at least one 5' adapter to the second reaction composition comprising double-stranded adapter-oligonucleotide duplexes and first ligation products and incubating under conditions suitable for forming at least some second ligation products, thereby reducing adapter-dimer formation.

BRIEF DESCRIPTION OF THE FIGURES

These and other features and advantages of the current teachings will become better understood with regard to the following description, appended claims, and accompanying figures. The skilled artisan will understand that the figures, described below, are for illustration purposes only. The figures are not intended to limit the scope of the disclosed teachings in any way.

FIGS. 4A-4B depicts exemplary PAGE images of samples that could be size selected with Gel-Free Size Selection Cleanup (FIG. 4A) or PAGE Size Selection and Cleanup (FIG. 4B), as described in Certain Exemplary Techniques.

FIG. 6 depicts technical duplicates of various reaction compositions generated using exemplary methods analyzed on a 6% TBE-PAGE gel, stained with SYBR® Gold. Lanes 1-4 depict small RNA libraries prepared with annealing of the RT primer to the 3' adapter prior to the 3' ligation step, and lanes 5-8 depict small RNA libraries prepared with annealing of the RT primer to the 3' adapter after to the 3' ligation step. Lanes 1, 2, 5, and 6 depict libraries where an exemplary end-fill method was used; lanes 3, 4, 7, and 8 depict libraries where no end-fill method was not used; lanes marked M contain a base pair ladder standard. (+EF: an illustrative end-fill method of the current teachings was used in generating these samples; –EF: no end-fill technique was employed with these samples; Pre-anneal: oligonucleotide/RT primer annealed with 3' adapter prior to use; Post-anneal: oligonucleotide added to reaction composition after 3' adapter ligation).

FIG. 7 depicts technical duplicates of various reaction compositions generated using exemplary methods analyzed on a 6% TBE-PAGE gel, stained with SYBR Gold. Lanes 1 and 2 depict libraries created using an exemplary end-fill method comprising the an embodiment of disclosed excess 3' adapter removal technique. Lanes 3 and 4 depict libraries created using an embodiment of the disclosed end-fill method but not an excess 3' adapter removal technique; lane M contains a base pair ladder standard. All libraries shown in this figure were constructed with adapters and primers that are compatible with Ion Torrent-based sequencing.

DETAILED DESCRIPTION OF CERTAIN EXEMPLARY EMBODIMENTS

Figure 1:
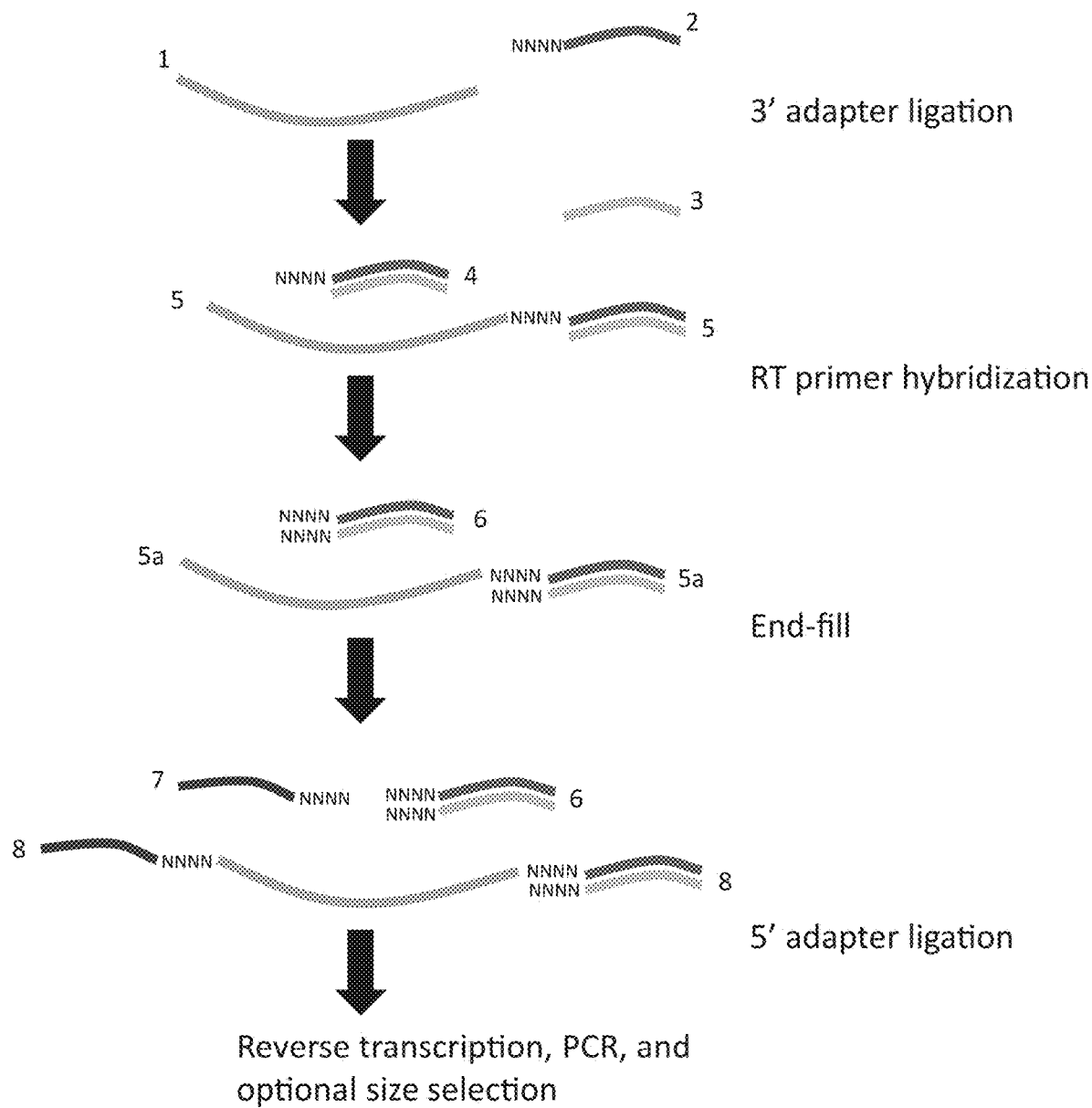
FIG. 1 schematically depicts certain exemplary methods for reducing adapter dimer formation.

It is to be understood that both the foregoing general description and the following detailed descriptions are illustrative and exemplary only and are not intended to limit the scope of the disclosed teachings. The section headings used herein are for organizational purposes only and are not to be construed as limiting the subject matter of the disclosed teachings.

In the Summary above, the Detailed Description, the accompanying figures, and the claims below, reference is made to particular features (including method steps) of the current teachings. It is to be understood that the disclosure in this specification includes possible combinations of such particular features. For example, where a particular feature is disclosed in the context of a particular embodiment of the current teachings, or a particular claim, that feature can also be used, to the extent possible, in combination with and/or in the context of other particular embodiments, and in the current teachings in general.

Where reference is made to a method comprising two or more combined steps, the defined steps can be performed in any order or simultaneously (except where the context excludes that possibility), and the method include one or more other steps which are carried out before any of the defined steps, between two of the defined steps, or after all of the defined steps (except where the context excludes that possibility).

In this specification, certain U.S. patents, U.S. patent applications, and other documents may have been incorporated by reference. The text of such U.S. patents, U.S. patent applications, and other materials is, however, only incorporated by reference to the extent that no conflict exists between such text and the description and drawings set forth in this specification. In the event of such conflict, then any conflicting material in any incorporated by reference U.S. patents, U.S. patent applications, and other materials is specifically not incorporated by reference in this specification.

Definitions

As used herein, the term "comprising", which is synonymous with "including", and cognates of each (such as comprise, comprises, include, and includes), is inclusive or open-ended and does not exclude additional unrecited components, elements, or method steps, that is other components, steps, etc., are optionally present. For example but not limited to, an article "comprising" components A, B, and C may consist of (that is, contain only) components A, B, and C; or the article may contain not only components A, B, and C, but also one or more additional components.

An "oligonucleotide" of the current teachings means a nucleic acid molecule that may serve as a binding site for a reverse transcription primer (RT primer) or the complement of an RT primer binding site. The oligonucleotides of the current teachings may have differing lengths.

Terms such as "randomized bases", "randomized nucleotides" random bases" and "random nucleotides" refer to a nucleic acid sequence that is created with a random sequence, in contrast to a sequence that is designed to specifically hybridize to a target or desired nucleotide sequence. In certain embodiments, a plurality of different oligonucleotides comprise the same core sequence (i.e., the complement of a sequence of interest) but differing randomized ends. For example but not limited to, a series of 3' adapters with a core sequence that is the complement of at least a portion of the sequence of the oligonucleotide of the current teachings, but different 5' randomized ends of between 1 and 25 nucleotides. In certain embodiments, randomized bases are present at the 5' end of 3' adapters, the 3' end of 5' adapters, or both.

The term "small RNA" as used herein, refers to various species of RNA known in the art, typically 15-45 nucleotides long. Examples of small RNAs include microRNA (miRNA), small interfering RNA (siRNA), small nuclear RNA (snRNA), small nucleolar RNAs (snoRNAs), Piwi-interacting RNA (piRNA), and bacterial small RNA.

Figure 2:
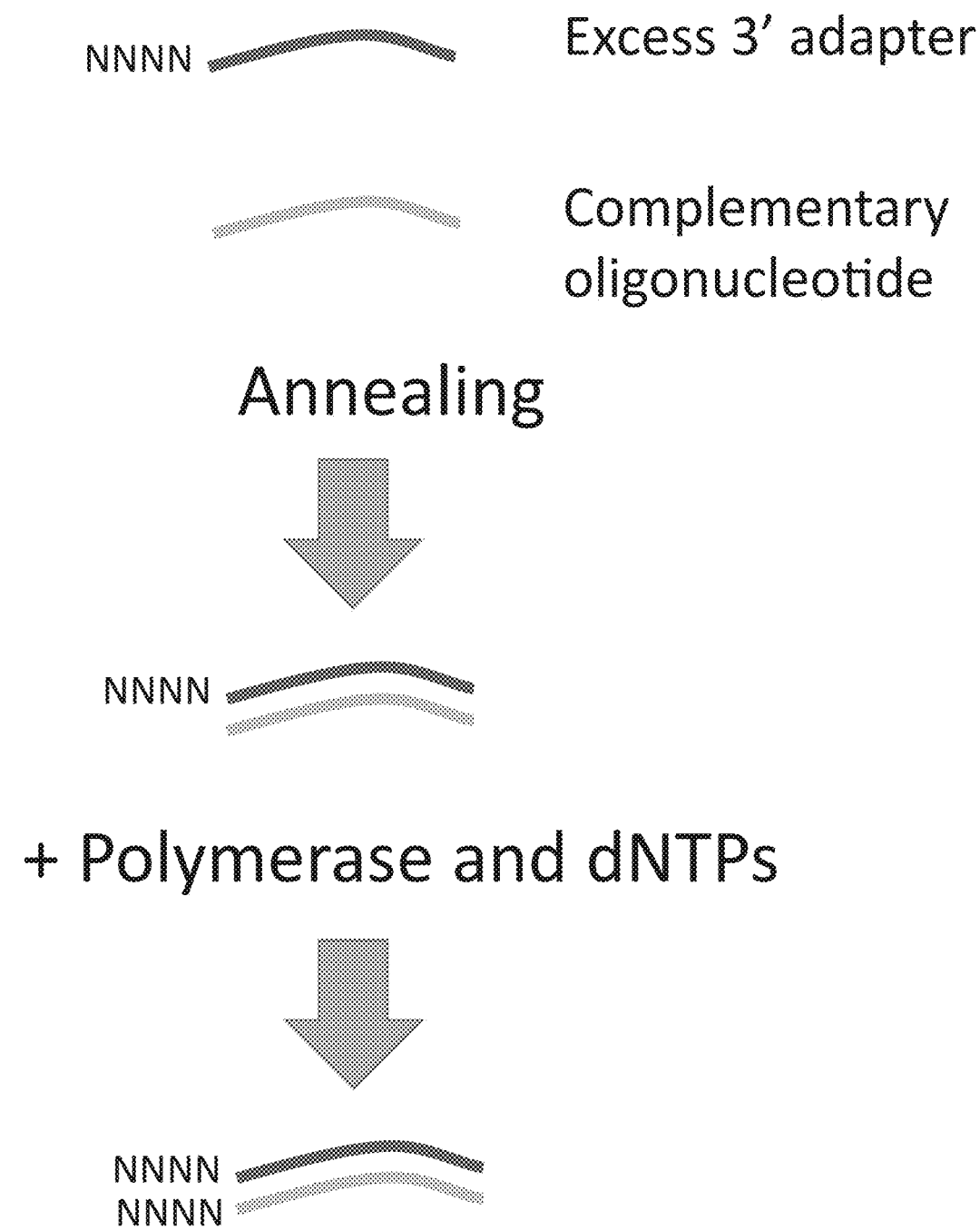
FIG. 2 schematically depicts an exemplary end-filling embodiment for converting excess 3' adapter into blunt-ended dsDNA.

FIG. 1 provides a schematic overview of certain exemplary methods of the current teachings. Target nucleic acids 1 are combined with suitable 3' adapters 2 comprising random nucleotides (indicated by NNNN) at the 5' end (FIG. 1, 3' adapter ligation). In the presence of a suitable ligase and under appropriate conditions, first ligation products, also known as 3' ligation products, are formed (each comprising a 3' adapter comprising random 5' nucleotides 2 ligated to target nucleic acids 1). Oligonucleotides comprising a sequence suitable for binding a reverse transcription primer 3 are added to the reaction composition comprising the first ligation products and un-ligated 3' adapters 2 and incubated under conditions suitable for the oligonucleotides 3 to anneal with the first ligation products (FIG. 1, RT primer hybridization). Duplexes are formed comprising: first ligation product-primer duplexes, comprising single and double-stranded portions 5; and adapter-oligonucleotide duplexes, a primarily double-stranded complex comprising a single-stranded 5' overhang 4. In the presence of at least one suitable polymerase and under appropriate conditions, end-filling occurs, resulting in the formation of a double-stranded complex 6 that is generated when the polymerase "end fills" the 5' overhang of the primarily double-stranded complex comprising a single-stranded 5' overhang 4 (FIG. 1, End-fill; FIG. 2). Next, 5' adapters comprising random nucleotides (shown as NNNN) on their 3' ends 7 are combined with the reaction composition comprising first ligation products which have been end-filled 5a and the double-stranded and end-filled adapter-oligonucleotide duplexes 6 and in the presence of a suitable ligase and under suitable conditions for second ligation products 8 (each comprising a 5' adapter, a target nucleic acid, and a 3'adapter with an annealed oligonucleotide) to be formed (FIG. 1, 5' adapter ligation).

Figure 3:
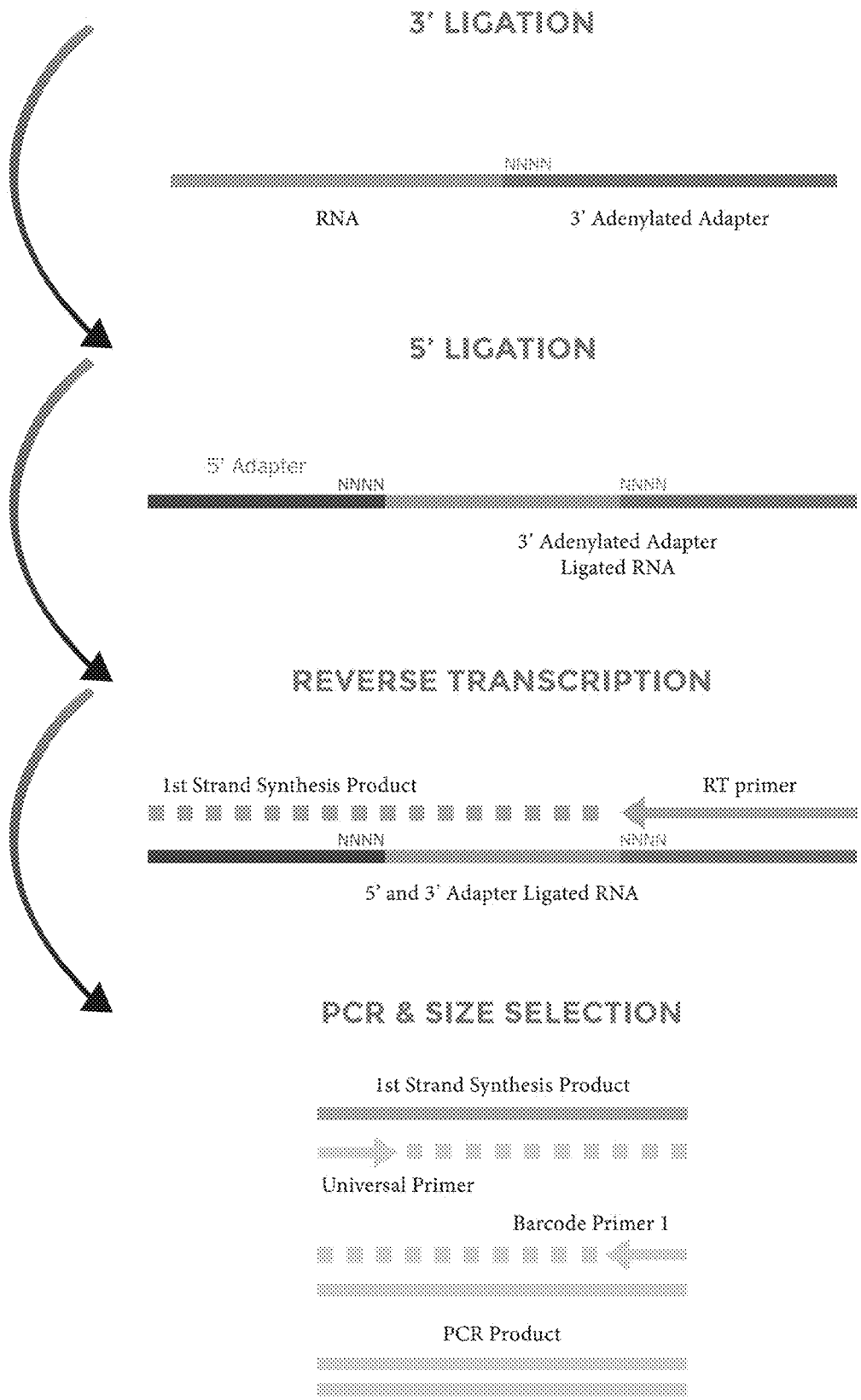
FIG. 3 schematically depicts on overview of an exemplary sRNA-seq library construction protocol of the current teachings comprising adapters with randomized ends.

In certain embodiments, total RNA in nuclease-free water is used for preparing sRNA-library using certain disclosed methods and kits. This RNA is combined with at least one pool of pre-adenylated ssDNA 3' adapters comprising random nucleotides at the 5' end, reaction buffer, and truncated T4 RNA ligase 2 enzyme, and incubated under conditions suitable for ligation of the adapter to the 3' and of small RNA molecules. The nucleic acid in the reaction composition is obtained using a combination of SPRI magnetic beads and isopropanol, and the products eluted in nuclease-free water. Next, at least one pool of ssDNA oligonucleotides that comprise an RT primer binding site are annealed to both excess 3' adapters (that which was not ligated to a small RNA molecule) and 3' adapter that has been ligated to a small RNA molecule. The annealing of this oligonucleotide to excess 3' adapter results in the formation of a double stranded DNA molecule with a 5' overhang (see 4 in FIG. 1; FIG. 2). Buffer, dNTPs, and a suitable DNA polymerase, such as T4 DNA polymerase, are added and the reaction mixture is incubated under conditions suitable for polymerization, resulting in DNA polymerization on the 3' end of the oligonucleotide using the random bases of the 3' adapter as a template (depicted schematically in FIG. 1 End-fill; FIG. 2). The reaction mixture is then incubated under conditions suitable to inactivate the T4 DNA polymerase enzyme. The typical components of a 5' ligation reaction, including the ssRNA 5' adapter, buffer, ATP, and T4 RNA ligase 1, are then added and the reaction mixture is incubated under conditions suitable for RNA ligation, resulting in ligation of 5' adapter to the 5' end of small RNA molecules. However, excess 3' adapter that was converted into blunt-ended dsDNA by the end-filling process (e.g., 6 in FIG. 1) is a poor substrate for the at least one second ligase, for example T4 RNA ligase 1, resulting in significant reduction in adapter-dimer formation compared to results obtained not using the methods of the current teachings. The library preparation process may be completed according to various sRNA-seq library preparation protocols, including for example reverse transcription, PCR amplification and gel purification or other size selection protocol, including the schematic depiction in FIG. 3.

According to certain disclosed methods, an end-filling technique is combined with a technique for removing excess 3' adapter, for example as provided in the NEXTFLEX Small RNA Sequencing Kit (Bioo Scientific), to further reduce formation of adapter-dimer products.

In some embodiments, the oligonucleotide is annealed to the 3' adapter prior to, during, or after the 3' ligation reaction.

In some embodiments, the length of the randomized portion of the 3' adapter (shown schematically in FIG. 1 as NNNN) may be between 1-25 nucleotides; the length of the randomized portion of the 5' adapter (shown schematically in FIG. 1 as NNNN) may be between 1-25 nucleotides; or the randomized portions of the 3' adapters and the 5' adapters may be between 1-25 nucleotides.

In some embodiments, the oligonucleotide may not be the same length as the non-randomized portion of the 3' adapter. In certain embodiments, a 3' adapter comprises an activated adenylation (rApp) at its 5' end, a dideoxynucleotide at its 3' end, or an activated adenylation (rApp) at its 5' end and a dideoxynucleotide at its 3' end. In certain embodiments, a 3' adapter comprises four random nucleotides immediately internal to the activated adenylation (rApp) at its 5' end (5'rAppNNNN-) and the 5' adapter comprises four random nucleotides at its 3' end. In certain embodiments, the 5' adapter comprises RNA. In certain embodiments, the RT primer comprises a barcode sequence. In certain embodiments, a multiplicity of different RT primers are employed, wherein the RT primers comprise different barcodes sequences to facilitate multiplexed sequencing, for example but not limited to low-level multiplexing.

In some embodiments, the oligonucleotide may contain a 5' overhang region.

Certain methods and kits of the current teachings comprise at least one DNA polymerase. Those in the art will appreciate that a wide variety of prokaryotic and eukaryotic DNA polymerases, both thermo-labile and thermostable, as well as many viral DNA polymerases are suitable for use in the disclosed methods and kits. Exemplary DNA polymerases include T4 DNA Polymerase, Taq polymerase, human DNA polymerase alpha, Moloney Murine Leukemia Virus Reverse Transcriptase (M-MLV RT), and *E. coli* DNA Pol I (including Klenow fragment).

Certain methods and kits of the current teachings comprise at least one first ligase and at least one second ligase. In certain embodiments, the first ligase and the second ligase are the same, for example, two aliquots of T4 RNA ligase 1 added to separate steps of certain method embodiments. Those in the art will appreciate that a wide variety of prokaryotic and eukaryotic ligases, both thermo-labile and thermostable, as well as many viral DNA ligases are suitable for use in the disclosed methods and kits. Exemplary ligases for use in certain disclosed methods and kits include T4 RNA ligase 1, *Methanobacterium thermoautotrophicum* thermostable RNA ligase, CircLigase™ RNA Ligase (Epicentre, Madison, Wis.), T4 RNA ligase 2 (including truncation mutants and point mutants thereof), eukaryotic tRNA ligase, *E. coli* RNA ligase RtcB, and T4 DNA ligase.

According to certain embodiments, at least some oligonucleotides and at least some 3' adapters are annealed prior to 3' ligation. In certain embodiments, such pre-annealed complexes are stored for later use.

Certain Exemplary Techniques

Best results are obtained with high quality starting material. The use of degraded RNA may result in poor yields or lack of sequencing output data. The inventors recommend running total RNA on a 1-2% agarose gel or examining its integrity using an Agilent Bioanalyzer. High quality total RNA preparations should have a 28S band that is twice as intense as the 18S band of ribosomal RNA. At low concentrations, small RNA is difficult to detect on a gel; however, it can be detected using an Agilent Bioanalyzer Small RNA assay. For low input library preparation, the inventors recommend diluting the NEXTFLEX™ 3' 4N Adenylated Adapter and the NEXTFLEX™ 5' 4N adapter 1/2 to 1/4 with nuclease-free water.

TABLE 1

According to certain embodiments of the current teachings, the following information may be helpful.

| Sample Input | Adapter dilution | PCR cycles | Gel-Free Size Selection |
|---|---|---|---|
| 2 μg-200 ng | None | 12-18 | + |
| 200 ng-50 ng | ½-¼ | 16-22 | +/− |
| 50 ng-5 ng | ¼-⅛ | 22-25 | − |

For illustration purposes, the following exemplary techniques may be performed using the NEXTFLEX™ Small RNA-Seq Kit v3. Those in the art will appreciate that the principals of these exemplary techniques are broadly applicable and that suitable reagents and components for performing these methods are available from various commercial sources.

3' NEXTFLEX™ 4N Adenylated Adapter Ligation. Allow 50% PEG to come up to room temperature before use. For each sample, combine the following reagents on ice in a nuclease-free 96-well PCR plate: _μL RNA+_μL Nuclease-free Water=10.5 μL. Heat at 70° C. for 2 minutes then immediately place on ice. Incubate on ice for 2-5 minutes. For each sample, combine the following reagents on ice in a nuclease-free 96-well PCR plate: 10.5 μL RNA (in Nuclease-free Water), 5 μL 50% PEG, 1 μL 3' NEXTFLEX 4N Adenylated Adapter (up to 1/4 dilution may be used), 2 μL AIR Ligase buffer, 0.5 μL RNase Inhibitor, and 1 μL AIR Ligase. Mix thoroughly by pipetting until homogenous. Incubate at 22° C. for 2 hours in a thermocycler. For ligations to 2' O-methylated small RNAs, such as those found in plants, incubate at 16° C. overnight. Proceed immediately to next Excess 3' Adapter Removal technique.

Excess 3' Adapter Removal. To each sample, add 20 μL of Adapter Depletion Solution and mix well by pipette. Add 40 μL of NEXTFLEX™ Cleanup Beads and mix well by pipette. Add 60 μL of isopropanol and mix well by pipette. Incubate for five minutes. Place the reaction composition near a magnetic field for 5 minutes or until the composition appears clear. Remove and discard supernatant. Add 180 μL of freshly prepared 80% ethanol, incubate for 30 seconds, and remove all of the supernatant. Repeat this step for a total of 2 ethanol washes. IMPORTANT: Always use freshly prepared 80% ethanol and do not incubate the bead pellet with 80% ethanol for extended periods. Incubate sample for 3 minutes. After one minute, remove all residual liquid that may have collected at the bottom of the well. Remove the composition from the magnetic field and resuspend bead pellet in 22 μL of Resuspension Buffer by pipetting volume up and down. Ensure that beads are completely resuspended. Incubate for two minutes. Place the reaction composition near a magnetic field for 3 minutes or until the composition appears clear. Transfer 20 μL of supernatant to a new well. Add 20 μL of Adapter Depletion Solution and mix well by pipette. Add 40 μL of NEXTFLEX Cleanup Beads and mix well by pipette. Add 60 μL of isopropanol and mix well by pipette. Incubate for 5 minutes. Place the reaction composition near a magnetic field for 5 minutes or until the composition appears clear. Remove and discard supernatant. Add 180 μL of freshly prepared 80% ethanol, incubate for 30 seconds, and remove all of the supernatant. Repeat this step for a total of 2 ethanol washes. Always use freshly prepared 80% ethanol and do not incubate the bead pellet with 80% ethanol for extended periods. Incubate sample for 3 minutes. After one minute, remove any residual liquid that may have collected at the bottom of the well. Remove composition from the magnetic field and resuspend bead pellet in 13 µL of Nuclease-free Water by pipetting. Ensure that beads are completely resuspended. Incubate for two minutes. Place the reaction composition near a magnetic field for 3 minutes or until the composition appears clear. Transfer 11.5 µL of supernatant to a new well. Either proceed to the end-filling technique or store the compositions overnight at −20° C., then thaw compositions on ice before proceeding. Throughout the application reference is made to placing a reaction composition near a magnetic field or removing a reaction composition from the magnetic field and similar terminology. It is to be understood that the composition may be transported to or from the vicinity of the magnetic field or the magnetic field may be transported to and or removed from the vicinity of the composition.

Excess Adapter Inactivation (End-filling). For each sample, combine the following reagents on ice in a nuclease-free 96 well PCR plate: 11.5 µL Purified 3' NEXTFLEX™ 4N Adenylated Adapter Ligated RNA (from previous Excess 3' Adapter Removal technique), 1.5 µL Adapter Inactivation Reagent 1, 0.5 µL Adapter Inactivation Reagent 2, and 0.5 µL Adapter Inactivation Enzyme (total volume 14 µL). Mix thoroughly by pipetting, then incubate for 15 minutes at 12° C., 20 minutes at 50° C., the place at 4° C.

5' NEXTFLEX™ 4N Adapter Ligation. Heat 1.5 µL of 5' NEXTFLEX 4N adapter per reaction at 70° C. for 2 minutes, then immediately place on ice. For each sample, combine the following reagents on ice in a nuclease-free 96 well PCR plate: 14 µL Purified 3' NEXTFLEX™ 4N Adenylated Adapter Ligated RNA (from previous step), 4.5 µL 50% PEG, 1.5 µL 5' NEXTFLEX™ 4N Adapter (Up to 1/4 dilution may be used, 1.5 µL AIR Ligase Buffer, 1.5 µL ATP, 0.5 µL RNA Inhibitor, 1.5 µL RNA Ligase 1 (total volume 25 µL). Mix thoroughly by pipetting, incubate at 20° C. in a thermocycler, then proceed with next step. Alternatively, the samples may be stored overnight at −20° C.

Reverse Transcription-First Strand Synthesis. For each sample, combine the following reagents on ice in a nuclease-free 96 well PCR plate: 25 µL 5' and 3' NEXTFLEX™ Adapter Ligated RNA, 5 µL Nuclease-free Water, 4 µL 10×M-MuLV Buffer (vortex prior to use to dissolve precipitate), 4 µL dNTPs, and 2 µL M-MuLV Reverse Transcriptase (total volume 40 µL). Mix thoroughly by pipetting. Incubate 30 minutes at 42° C., 10 minutes at 90° C., then proceed to next step.

Bead Cleanup. To each sample, add 20 µL of NEXTFLEX™ Cleanup Beads and mix well by pipette. Add 22 µL isopropanol and mix well by pipette. Incubate for 5 minutes. Place the reaction composition near a magnetic field for 5 minutes or until the composition appears clear. Transfer 75 µL of supernatant to a new well. The supernatant solution contains the cDNA product. Take care to not transfer beads along with clear supernatant. Remove the composition from the magnetic field add 10 µL Adapter Depletion Solution and mix well by pipette. Add 20 µL of NEXTFLEX™ Cleanup Beads and mix well by pipette. Place the solution near a magnetic field for 5 minutes or until the solution appears clear. Remove and discard supernatant. Add 180 µL of freshly prepared 80% ethanol, incubate for 30 seconds, then remove all of the supernatant. Repeat this step for a total of 2 ethanol washes. Incubate sample for 3 minutes. After one minute, remove all residual liquid that may have collected at the bottom of the well. Remove the plate from magnetic field and resuspend bead pellet in 20 µL Nuclease-free Water by pipetting volume up and down. Ensure that beads are completely resuspended. Incubate for 2 minutes. Place the plate near a magnetic field for 3 minutes or until the composition appears clear. Transfer 18 µL of supernatant to a new well and proceed to PCR amplification. Alternatively, the samples can be stored overnight at −20° C. Frozen samples should be thawed on ice before proceeding.

PCR Amplification. For each sample, combine the following reagents on ice in a nuclease-free 96 well PCR plate: 18 µL Purified First Strand Synthesis Product, 1 µL NEXTFLEX™ universal primer, 1 µL NEXTFLEX™ barcoded primer, and 5 µL NEXTFLEX™ Small RNA PCR Master Mix. The plate is placed in a thermocycler heated to over 80° C. and heated to 95° C. for two minutes, cycled 12-25 cycles of 95° C. for twenty seconds—60° C. for thirty seconds—72° C. for fifteen seconds, then two minutes at 72° C. The PCR amplified product is then size selected.

| Oligonucleotide Sequences: | |
|---|---|
| 3' NEXTFLEX 4N Adenylated Adapter | 5' rApp-NNNNTGGAATTCTCGGGTGCCAAGG-3ddC (SEQ ID NO: 1) |
| 5' NEXTFLEX 4N Adapter | 5' GUUCAGAGUUCUACAGUCCGACGAUCNNNN (SEQ ID NO: 2) |
| NEXTFLEX RT Primer | 5' GCCTTGGCACCCGAGAATTCCA (SEQ ID NO: 3) |
| NEXTFLEX Barcode Primer | 5' CAAGCAGAAGACGGCATACGAGATXXXXXXGTGAC TGGAGTTCCTTGGCACCCGAGAATTCCA (SEQ ID NO: 4; where XXXXXX = barcode index region-see below) |
| NEXTFLEX Universal Primer | 5' AATGATACGGCGACCACCGAGATCTACACGTTCAGA GTTCTACAGTCCGA (SEQ ID NO: 5) |
| microRNA Control | 5' Phos-CUCAGGAUGGCGGAGCGGUCU 3' (SEQ ID NO: 6) |

Exemplary Barcode Index Region Sequences: CGTGAT, ACATCG, GCCTAA, TGGTCA, CAGTGT, ATTGGC, GATCTG, TCAAGT, CTGATC, AAGCTA, GTAGCC, TACAAG, TTGACT, GGAACT, TGACAT, GGACGG, CTCTAC, GCGGAC, TTTCAC, GGCCAC, GGAAAC, CGTACG, CCACTC, GCTACC, ATCAGT, GCTCAT, AGGAAT, CTTTTG, TAGTTG, CCGGTG, ATCGTG, TGAGTG, CGCCTG, GCCATG, AAAATG, TGTTGG, ATTCCG, AGCTAG, GTATAG, TCTGAG, GTCGTC, CGATTA, GCTGTA, ATTATA, GAATGA, TCGGGA, CTTCGA, and TGCCGA.

Determining which Size Selection Method to Use. Typically, gel-free library preparation can be achieved with 200 ng-2 µg of total RNA starting material and 18 or fewer cycles of PCR. PAGE-based size selection will be necessary when using less than 200 ng of total RNA starting material and up to 25 cycles of PCR. However, the small RNA fraction of total RNA can vary greatly depending on the cell/tissue type and the extraction method used, so it is the user's responsibility to determine optimal input amounts and PCR cycle numbers. Following PCR, products may be analyzed by TBE-PAGE gel, Agilent Bioanalyzer HS DNA Assay, or similar technique. For analysis by PAGE gel, we recommend mixing 5 µL of PCR product with 1 µL of NEXTFLEX Loading Dye and running on a 6% TBE-PAGE gel alongside 5 µL of Ready to Load Low Molecular Weight Ladder, and staining with SYBR Gold or ethidium bromide. For analysis by Bioanalyzer, we recommend running 1 µL of PCR product diluted 1/4 with nuclease-free water. The Bioanalyzer software may not correctly identify the peak sizes, so it is recommended to also run a library created with miRNA Control to help identify the ~150 bp peak. Presence of a strong ~150 bp band indicates a successful library preparation, and absence of a band ~130 bp indicates that gel-free size selection may be used. See Table 2.

TABLE 2

| ~150 bp band | ~130 bp band | Size Selection Method |
| --- | --- | --- |
| Strong | Absent or very weak | Gel-free size selection |
| Strong | Weak | PAGE size selection or repeat experiment with fewer PCR cycles |
| Strong | Strong | PAGE size selection |
| Absent/Weak | Absent | Additional PCR cycles |
| Absent/Weak | Strong | Repeat experiment with adapter dilution (½-¼) and with additional PCR cycles |

Gel-Free Size Selection & Cleanup. Ensure the volume of all samples is 25 µL. If less, add Nuclease-free Water to bring the entire volume up to 25 µL. Add 32.5 µL of NEXTFLEX™ Cleanup Beads and mix well by pipetting. Incubate for 5 minutes. Place the samples near a magnetic field for 5 minutes or until the solution appears clear. Transfer 52.5 µL of supernatant to a new well. The supernatant contains the amplified product. Take care to not transfer beads along with clear supernatant. Remove the samples from the magnetic field. Add 30 µL of NEXTFLEX™ Cleanup Beads to each sample and mix well by pipette. Incubate five minutes. Place the samples near a magnetic field for 5 minutes or until the solution appears clear. Remove and discard supernatant. Add 180 µL of freshly prepared 80% ethanol, incubate for 30 seconds, and remove all of the supernatant. Repeat this step for a total of 2 ethanol washes. Incubate sample for 3 minutes. After one minute, remove all residual liquid that may have collected at the bottom of ension Buffer by pipetting volume up and down. Ensure that beads are completely resuspended. Incuthe well. Remove plate from magnetic field and resuspend bead pellet in 13.5 µL of Resuspbate for two minutes. Place the samples near a magnetic field for 3 minutes or until the solution appears clear. Transfer 12 µL of supernatant to a new well or a clean microcentrifuge tube. This is your sequencing library. Check the size distribution of the final library by Bioanalyzer High Sensitivity DNA Assay (Agilent) and the concentration by Qubit dsDNA HS Assay (Life Technologies).

PAGE Size Selection & Cleanup. Add 5 µL of NEXTFLEX™ 6X Gel Loading Dye to each PCR product and mix well. Load purified PCR products onto a 6% TBE-PAGE gel. The inventors recommend leaving 1-2 lanes between samples prepared with the same barcode primer to avoid cross contamination. Samples prepared with different barcodes and that will be sequenced together may be run in adjacent lanes. In an adjacent lane, load 10 µL of Ready to Load Low MW Ladder. Run the gel with 1×TBE buffer at 200 V until the lower dye band is near the bottom of the gel (0.5-1 cm). The gel should run for approximately 30 minutes. Run times may vary depending on individual equipment. Carefully remove the gel from the glass plates and stain with a nucleic acid stain such as SYBR® Gold (Invitrogen) per manufacturer instructions. Visualize gel bands on a UV transilluminator or other gel documentation instrument. Using a clean razor, cut out the ~150 bp band and place into clean 1.7 mL tube. Do not cut out the ~130 bp band; this is adapter dimer product (see FIG. 4). The ladder band at 200 bp is twice as intense as the other bands and can be used for orientation. Briefly centrifuge the microcentrifuge tube containing the gel slice to collect the gel slice at the bottom of the tube. Crush the gel slice thoroughly with a disposable pestle. Leave the pestle in the tube. Add 300 µL of Elution Buffer to each tube and then remove the pestle, ensuring that as much gel as possible has been washed from the pestle. Let gel pieces soak at least 2 hours or overnight at room temperature with agitation. Do not incubate longer than overnight. Pulse spin tubes to collect all eluate from wall and lid. Carefully transfer the eluate (including crushed gel) to the top of a Spin-X Centrifuge tube (Sigma). Cutting the end off of a P1000 tip can help for transfers of larger gel pieces. Centrifuge the Spin-X tube at 16,000×g for 2 minutes. Dispose of the spin filter. Add 50 µL NEXTFLEX Cleanup Beads and 350 µL isopropanol to each tube and mix well. Incubate at room temperature for 10 minutes. Agitation during this incubation may increase efficiency of recovery. Pulse spin tubes to collect solution from walls and lid of tube and to pellet beads. Place the samples near a magnetic field for 2 minutes or until the solution appears clear. Carefully remove and discard fluid. Add 950 µL 80% ethanol, incubate for 30 seconds, then remove all of the supernatant. Repeat this step for a total of two ethanol washes. Dry samples for 3 minutes. After one minute, remove all residual liquid that may have collected at the bottom of the tube. Remove the plate from the magnetic field and resuspend bead pellet in 13 µL of Resuspension Buffer by pipetting volume up and down. Ensure that beads are completely resuspended and rehydrated. Incubate for 2 minutes. Place the samples near a magnetic field for 3 minutes or until the solution appears clear. Transfer 12 µL of supernatant to a clean 1.7 mL tube. This is your sequencing library. Check the size distribution of the final library by Bioanalyzer High Sensitivity DNA Assay (Agilent) and the concentration by Qubit dsDNA HS Assay (Life Technologies).

Certain Exemplary Embodiments

Example 1 Construction of an exemplary sRNA-seq library. In an exemplary method embodiment, sRNA-seq libraries were prepared from human brain total RNA (Ambion, cat. #AM7962) using the NEXTFLEX™ Small RNA Sequencing Kit v2 according to manufacturer's instructions, except as indicated. For sRNA-seq libraries prepared according to certain disclosed methods, following Excess 3' Adapter Removal using NEXTFLEX™ beads, 11.5 µL supernatant of nuclease free water containing 3' ligation products was recovered. To each supernatant 1.5 µL of NEBuffer 2.1 (500 mM NaCl, 100 mM Tris-HCl, 100 mM MgCl2, 1 ng/ml BSA, pH 7.9), 0.5 uL of 6.25 uM dNTPs, and 0.5 uL of T4 DNA Polymerase (Enzymatics, Cat. # P7080L) were added and incubated at 12° C. for 15 minutes followed by 50° C. for 20 minutes. The following modifications were then made to the NEXTFLEX™ Small RNA sequencing kit v2 protocol: 1) in the 5' adapter ligation step, samples were not heated at 70° C. for 2 minutes. Instead, the 5' 4N adapter was heated separately at 70° C. for 2 minutes and then added to the reaction. 2) In the 5' adapter ligation step, 4.5 µL of 50% PEG was added instead of 3.5 µL. 3) In the reverse transcription step, 5 µL of nuclease-free water was added instead of 8. 4) In order to compare yields and adapter-dimer content of different conditions, 5 µL of a the 25 µL PCR reaction was run on a 6% TBE-PAGE gel, stained with SYBR® Gold, and visualized an a UV transilluminator.

Figure 5:
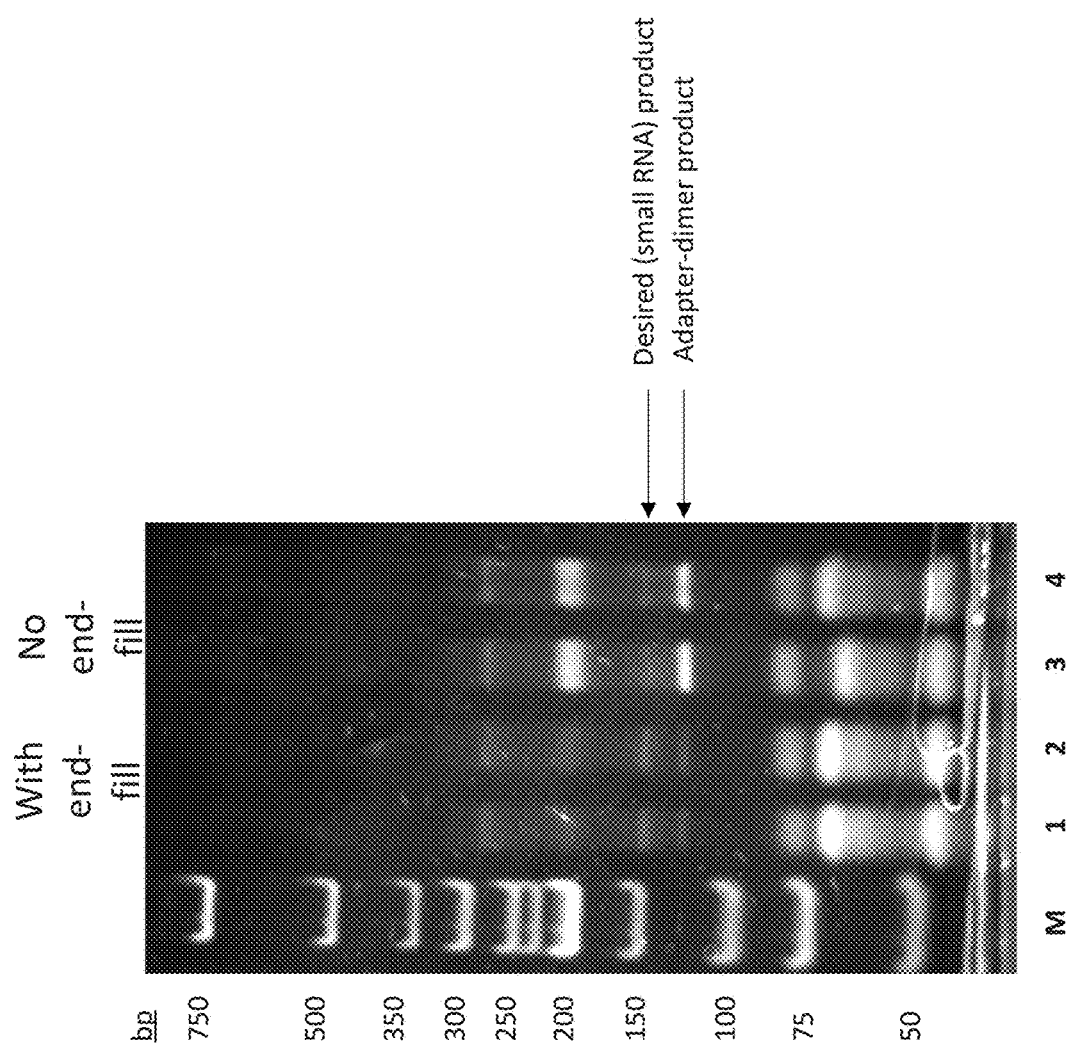
FIG. 5 depicts various reaction compositions generated using exemplary methods analyzed on a 6% TBE-PAGE gel, stained with SYBR® Gold. Lanes 1 and 2 are technical duplicates of small RNA libraries created using an exemplary end-fill method ("With end-fill") and lanes 3 and 4 are technical duplicates of small RNA libraries created without using an end-fill method of the current teachings ("No end-fill"); lane M contains a base pair ladder standard.

Example 2. Effectiveness of end-filling in reducing adapter-dimers. To show the effectiveness of the disclosed end-filling method, sRNA-seq libraries were prepared from 100 ng human brain total RNA, as described in Example 1, either with or without the described end-filling method and analyzed by TBE-PAGE (FIG. 5). Lanes 1 and 2 are technical duplicates of small RNA libraries created with the proposed end-fill method and lanes 3 and 4 are technical duplicates of small RNA libraries created without the end-fill method; lane M contains a base pair ladder standard. The results demonstrate that the method is not only effective in reducing adapter-dimer but surprisingly also increases yield of insert-containing product.

Example 3. Effectiveness of annealing RT-primer prior to 3' ligation. 3' adapter was pre-annealed to oligonucleotide and libraries were prepared from 100 ng human brain total RNA, as described in Example 1, using either the pre-annealed oligonucleotide-3' adapter duplexes or with the oligonucleotide annealed after 3' ligation. Referring to FIG. 6, lanes 1-4 depict small RNA libraries prepared with annealing of the oligonucleotide to the 3' adapter prior to the 3' ligation step ("Pre-anneal"); and lanes 5-8 depict small RNA libraries prepared by annealing the oligonucleotide to the 3' adapter after to the 3' ligation step ("Post-anneal"). Lanes 1, 2, 5, and 6 depict libraries prepared according to the current teachings; while the libraries depicted in lanes 3, 4, 7, and 8 depict libraries were prepared without the end-filling technique of the current teachings; lanes marked M contain a base pair ladder standard. The results demonstrate that pre-annealing the 3' adapter and the oligonucleotide does not significantly affect either efficiency of 3' adapter annealing to small RNA molecules or the effectiveness of the described method in reducing adapter-dimer formation.

Example 4. Combination with other adapter-dimer reduction strategies. To evaluate whether certain disclosed methods are even more effective in reducing adapter-dimer when combined with an excess adapter removal technique, we tested an exemplary method embodiment comprising an adapter-dimer reduction technique, Adapter Depletion Cleanup (ADC; also referred to as Excess 3' Adapter Removal, described above and also used in the NEXT-FLEX™ Small RNA Sequencing Kit (Bioo Scientific)). The ADC protocol involves mixing the sample with isopropanol, SPRI beads, and a depletion solution. This process allows depletion of unligated adapter while retaining larger ligation products, and is typically performed twice in succession. FIG. 7 shows the results obtained with libraries prepared from 500 ng of human brain total RNA using the ADC method alone, according to the NEXTFLEX™ Kit protocol [ADC (−) end-fill] or the ADC method combined with an exemplary end-fill method of the current teachings [ADC (+) end-fill].

All libraries shown in FIG. 7 were constructed using adapters and primers that are compatible with Ion Torrent-based sequencing platforms. These results show that combination of certain disclosed methods comprising end filling and ADC techniques depleted adapter-dimer product more effectively than methods comprising the ADC technique but not end filling. It should be noted that this experiment was performed with different 3' and 5' adapters and RT and PCR primers that result in desired products and adapter-dimer products of a different size than those in FIGS. 5 and 6.

Example 5. Use of an exemplary method with different 3' adapter sequences. The described methods should work regardless of the sequence of the "static" portion of the 3' adapter, so to test this the inventors used this method in sRNA-seq library construction using adapters that are compatible with either Illumina sequencing platforms or Life Technologies Ion Torrent platforms. FIG. 7 illustrates, among other things, that in certain exemplary method embodiments, the combination of end-filling with the ADC technique greatly reduces adapter-dimer formation in sRNA-seq libraries regardless of the adapter sequences used. All libraries shown in FIG. 7 were constructed with adapters and primers that are compatible with Ion Torrent-based sequencing. Lanes 1 and 2 of FIG. 7 depict libraries created using method embodiments comprising the end-fill technique combined with the ADC technique (ADC (+) end-fill). Lanes 3 and 4 of FIG. 7 depict libraries created using method embodiments comprising the end-fill technique but not the ADC technique (ADC (−) end-fill); lane M contains a base pair ladder standard. Thus, if the required adapter sequences change as sequencing technology advances, the current teachings may still be used to reduce adapter-dimer formation.

Certain Exemplary Kits

In certain embodiments, kits are provided to expedite the performance of various disclosed methods. Kits serve to expedite the performance of certain method embodiments by assembling two or more reagents and/or components used in carrying out certain methods. Kits may contain reagents in pre-measured unit amounts to minimize the need for measurements by end-users. Kit may also include instructions for performing one or more of the disclosed methods. In certain embodiments, at least some of the kit components are optimized to perform in conjunction with each other. Typically, kit reagents may be provided in solid, liquid, or gel form.

Certain kit embodiments comprise: at least one 3' adapter comprising 1-25 random bases on the 5' end, at least one oligonucleotide complementary to at least a portion of the 3' adapter, and at least one 5' adapter with 1-25 random bases on the 3' end, T4 RNA ligase 2, and T4 RNA ligase 1. Certain kit embodiments further comprise DNA polymerase, T4 ligase 1, T4 ligase 2 or DNA polymerase, T4 ligase 1, and T4 ligase 2. In certain kit embodiments, the DNA polymerase comprises T4 DNA polymerase.

Although the disclosed teachings have been described with reference to various applications, methods, and kits, it will be appreciated that various changes and modifications may be made without departing from the teachings herein. The foregoing examples are provided to better illustrate the present teachings and are not intended to limit the scope of the teachings herein. Furthermore, various presently unforeseen or unanticipated alternatives, modifications, variations or improvements therein may be subsequently made by those skilled in the art which are also intended to be encompassed by the following claims. Certain aspects of the present teachings may be further understood in light of the following claims.

What is claimed is:

1. A method for reducing adapter-dimer formation comprising:
   combining a sample comprising target small ribonucleic acids (RNA), at least one deoxyribonucleic acid (DNA) 3' adapter, and at least one first RNA ligase to form a first reaction composition;
   incubating the first reaction composition under conditions suitable for first ligation products to be generated, to form a second reaction composition comprising first ligation products and at least some un-ligated 3' adapters;
   combining at least one oligonucleotide comprising a reverse transcription priming site with the second reaction composition to form a third reaction composition;
   incubating the third reaction composition under conditions suitable for at least some of the oligonucleotides to anneal with at least some of the first reaction products and at least some of the un-ligated 3' adapters to form 3' adapter-oligonucleotide duplexes comprising a single-stranded 5' overhang portion;
   combining at least one DNA-dependent DNA polymerase to the third reaction composition and incubating under conditions suitable for the polymerase to convert at least some of the 3' adapter-oligonucleotide duplexes comprising single-stranded 5' overhang portions to double-stranded blunt ended adapter-oligonucleotide duplexes by end-filling;
   combining at least one second ligase and at least one 5' adapter to the third reaction composition comprising double-stranded adapter-oligonucleotide duplexes and first ligation products and incubating under conditions suitable for forming at least some second ligation products;
   combining at least one reverse transcriptase with the second ligation products to generate double-stranded second ligation products, thereby reducing adapter-dimer formation.

2. The method of claim 1, wherein the first ligase comprises T4 RNA ligase 2 or truncated T4 RNA ligase 2; the DNA-dependent DNA polymerase comprises T4 DNA polymerase; and the second ligase comprises T4 RNA ligase 1 or *Methanobacterium thermoautotrophicum* RNA ligase.

3. The method of claim 1, wherein the oligonucleotide is annealed to the 3' adapter prior to, during, or after ligating the 3' adapter to a target ribonucleic acid.

4. The method of claim 1 wherein the 3' adapter comprises 1-25 randomized bases at the 5' end.

5. The method of claim 1 wherein the 5' adapter comprises 1-25 randomized bases at the 3' end.

6. The method of claim 1, further comprising amplifying at least some of the double-stranded second ligation products to generate amplification products.

7. The method of claim 6, wherein the amplifying comprises Polymerase Chain Reaction (PCR).

8. The method of claim 6, further comprising separating at least some of the amplification products by size.

9. A method for reducing, adapter-dimer formation comprising:
   combining a sample comprising target small ribonucleic acids, at least one 3' adapter annealed to an oligonucleotide comprising a reverse transcription primer binding site, and at least one first ligase to form a first reaction composition, wherein the 3' adapter annealed with the oligonucleotide comprises a single-stranded 5' overhang portion;
   incubating the first reaction composition under conditions suitable for first ligation products to be generated, to form a second reaction composition comprising first ligation products and at least some un-ligated 3' adapters annealed to oligonucleotides;
   combining at least one DNA-dependent DNA polymerase with the second reaction composition and incubating under conditions suitable for the polymerase to convert at least some of the single-stranded 5' overhang portions of the 3' adapters annealed to the oligonucleotides to double-stranded blunt ended adapter-oligonucleotide duplexes lacking overhang portions by end-filling;
   combining at least one second ligase and at least one 5' adapter to the second reaction composition comprising double-stranded adapter-oligonucleotide duplexes and first ligation products and incubating under conditions suitable for forming at least some second ligation products,
   combining at least one reverse transcriptase with the second ligation products to generate double-stranded second ligation products,
   thereby reducing adapter-dimer formation.

10. The method of claim 9, wherein the first ligase comprises T4 RNA ligase 2 or truncated T4 RNA ligase 2; the DNA-dependent DNA, polymerase comprises T4 DNA polymerase; and the second ligase comprises T4 RNA ligase 1 or *Methanobacterium thermoautotrophicum* RNA ligase.

11. The method of claim 9 wherein the 3' adapter comprises 1-25 randomized bases at the 5' end.

12. The method of claim 9 wherein the 5' adapter comprises 1-25 randomized bases at the 3' end.

13. method of claim 9, further comprising amplifying ask least some of the double-stranded second ligation products to generate amplification products.

14. The method ref claim 13, wherein the amplifying comprises Polymerase Chain Reaction (PCR).

* * * * *

UNITED STATES PATENT AND TRADEMARK OFFICE
CERTIFICATE OF CORRECTION

PATENT NO. : 10,597,706 B2
APPLICATION NO. : 15/354491
DATED : March 24, 2020
INVENTOR(S) : Masoud Toloue et al.

It is certified that error appears in the above-identified patent and that said Letters Patent is hereby corrected as shown below:

In the Claims

Column 18, Line 67 Claim 10: Replace "DNA-dependent DNA, polymerase" with --DNA-dependent DNA polymerase--;

Column 19, Line 7 Claim 13: Replace "13. method" with --13. The method--;

Column 19, Line 7 Claim 13: Replace "ask" with --at--; and

Column 19, Line 10 Claim 14: Replace "ref" with --of--.

Signed and Sealed this
Second Day of June, 2020

Andrei Iancu
*Director of the United States Patent and Trademark Office*